US012778439B2

(12) United States Patent

Chang et al.

(10) Patent No.: US 12,778,439 B2

(45) Date of Patent: Nov. 3, 2026

(54) DETECTION SYSTEM AND DETECTION METHOD OF VITAL SIGN

(71) Applicant: TMY Technology Inc., Taipei City (TW)

(72) Inventors: Su-Wei Chang, Taipei City (TW); Hsuan-Hung Kuo, Taipei City (TW)

(73) Assignee: TMY Technolgy Inc., Taipei City (TW)

( * ) Notice: Subject to any disclaimer, the term of this patent is extended or adjusted under 35 U.S.C. 154(b) by 0 days.

(21) Appl. No.: 18/764,406

(22) Filed: Jul. 5, 2024

(65) Prior Publication Data

US 2025/0040824 A1 Feb. 6, 2025

(30) Foreign Application Priority Data

Aug. 4, 2023 (TW) ................................ 112129272

(51) Int. Cl.

*A61B 5/05* (2021.01)

*A61B 5/00* (2006.01)

(Continued)

(52) U.S. Cl.

CPC .............. *A61B 5/05* (2013.01); *A61B 5/6893* (2013.01); *H04L 5/0007* (2013.01); *H04L 27/38* (2013.01)

(58) Field of Classification Search

None

See application file for complete search history.

(56) References Cited

U.S. PATENT DOCUMENTS 9,549,691 B2 * 1/2017 Tran .................. A61B 5/02042

11,345,234 B2 5/2022 Kim (Continued)

FOREIGN PATENT DOCUMENTS

CN 111655135 9/2020

CN 113740835 12/2021

(Continued)

OTHER PUBLICATIONS

Antonio Lazaro et al., “Seat-Occupancy Detection System and Breathing Rate Monitoring Based on a Low-Cost mm-Wave Radar at 60 GHz”, IEEE Access, Aug. 16, 2021, pp. 115403-115414, vol. 9.

“Notice of allowance of Japan Counterpart Application”, issued on Mar. 25, 2025, p. 1-p. 3.

*Primary Examiner* — Yi-Shan Yang

(74) *Attorney, Agent, or Firm* — JCIPRNET

(57) ABSTRACT

A detection system and a detection method of vital sign are provided. The method includes: transmitting a first radio frequency (RF) signal and receiving a first radar signal corresponding to the first RF signal by a first radar; performing IQ-demodulation on the first radar signal to obtain a first receiving in-phase component and a first receiving quadrature component; performing a first convolution operation to the first receiving in-phase component and a first symbol and performing a multiply accumulate (MAC) operation to a first result of the first convolution operation to obtain a first accumulated value; performing a second convolution operation to the first receiving quadrature component and the first symbol and performing a MAC operation to a second result of the second convolution operation to obtain a second accumulated value; and generating a vital sign according to the first and the second accumulated value.

12 Claims, 7 Drawing Sheets

(51) Int. Cl.

| | |
|---|---|
| ***H04L 5/00*** | (2006.01) |
| ***H04L 27/38*** | (2006.01) |

(56) References Cited

U.S. PATENT DOCUMENTS

| | | | | |
|---|---|---|---|---|
| 2007/0177694 | A1* | 8/2007 | Okunev | H04L 27/14 375/333 |
| 2016/0374622 | A1 | 12/2016 | Lin et al. | |
| 2017/0036541 | A1 | 2/2017 | Brankovic et al. | |
| 2020/0317207 | A1* | 10/2020 | Sloushch | G01S 13/536 |
| 2021/0275035 | A1 | 9/2021 | Lu et al. | |
| 2023/0225626 | A1 | 7/2023 | Peng et al. | |
| 2024/0118403 | A1* | 4/2024 | Baba | A61B 5/1072 |

FOREIGN PATENT DOCUMENTS

| | | | |
|---|---|---|---|
| CN | 114296141 | 4/2022 | |
| CN | 114506335 | 5/2022 | |
| CN | 115429252 | 12/2022 | |
| EP | 3324201 | 5/2018 | |
| JP | 2020101528 | 7/2020 | |
| JP | 2020531063 | 11/2020 | |
| JP | 2022538427 | 9/2022 | |
| KR | 20080049697 | 6/2008 | |
| TW | 201901181 | 1/2019 | |
| TW | 202023469 | 7/2020 | |
| TW | 202031196 | 9/2020 | |
| WO | 2019122414 | 6/2019 | |
| WO | WO-2019122414 A1 * | 6/2019 | G01C 21/3407 |
| WO | 2022180655 | 9/2022 | |

* cited by examiner

DETECTION SYSTEM AND DETECTION METHOD OF VITAL SIGN

CROSS-REFERENCE TO RELATED APPLICATION

This application claims the priority benefit of Taiwan application serial no. 112129272, filed on Aug. 4, 2023. The entirety of the above-mentioned patent application is hereby incorporated by reference herein and made a part of this specification.

BACKGROUND

Technical Field

The disclosure relates to a detection system and a detection method, and in particular relates to a detection system and a detection method of a vital sign.

Description of Related Art

Vital sign detection technology may be used in fields such as healthcare, driving monitoring, or home care. A traditional vital sign monitoring system may measure the vital sign of a test subject through a wearable device, but the wearable device may cause discomfort to the test subject. In order to reduce the discomfort of the test subject, the current monitoring system is improved to use radio frequency signal to measure the vital sign of the test subject. However, the vital sign measured using radio frequency signal may be affected by factors such as local oscillator (LO) failure, in-phase and quadrature (IQ) deviation, IQ gain mismatch, or frequency mismatch, resulting in distortion.

SUMMARY

A detection system and a detection method of a vital sign, which may measure the vital sign of a test subject in a powered vehicle using a non-contact method, are provided.

A detection system of a vital sign of the disclosure is adapted for a powered vehicle and includes a first radar and a server. The server is communicatively connected to the first radar and configured to perform the following operation. A first radio frequency (RF) signal is transmitted and a first radar signal corresponding to the first radio frequency signal is received by a first radar, in which the first radio frequency signal includes a first transmitting in-phase component and a first transmitting quadrature component. IQ-demodulation is performed on the first radar signal to obtain a first receiving in-phase component and a first receiving quadrature component. A first convolution operation is performed to the first receiving in-phase component and a first symbol corresponding to the first transmitting quadrature component, and a first multiply accumulate (MAC) operation is performed to a first result of the first convolution operation to obtain a first accumulated value. A second convolution operation is performed to the first receiving quadrature component and the first symbol corresponding to the first transmitting quadrature component, and a second MAC operation is performed to a second result of the second convolution operation to obtain a second accumulated value. A first processed signal is generated according to the first accumulated value and the second accumulated value. A vital sign corresponding to the first radar is generated according to the first processed signal, and the vital sign is output, in which the first symbol of the first transmitting quadrature component is orthogonal to a transmitting in-phase symbol of the first transmitting in-phase component, and the first symbol is a symbol whose mean value is zero.

In an embodiment of the disclosure, the detection system further includes a second radar. The second radar is communicatively connected to the server, in which the server is further configured to perform the following operation. A second radio frequency signal is transmitted and a second radar signal corresponding to the second radio frequency signal is received by the second radar. Preprocessing is performed on the second radar signal to obtain a second processed signal. A vital sign is generated according to the first processed signal and the second processed signal.

In an embodiment of the disclosure, the server is further configured to perform the following operation. In response to a first power component of the first processed signal being greater than a threshold and a second power component of the second processed signal being less than or equal to the threshold, the second processed signal is subtracted from the first processed signal to obtain the vital sign corresponding to the first radar.

In an embodiment of the disclosure, the server is further configured to perform the following operation. The powered vehicle is communicatively connected with to obtain dashboard information, and a lookup table is queried according to the dashboard information to obtain a vibration frequency. The first processed signal is processed according to the vibration frequency to obtain the vital sign.

In an embodiment of the disclosure, the dashboard information includes engine speed.

In an embodiment of the disclosure, the first symbol of the first transmitting quadrature component of the first radio frequency signal and a second symbol of a second transmitting quadrature component of the second radio frequency signal are orthogonal to each other.

In an embodiment of the disclosure, the first radio frequency signal and the second radio frequency signal are orthogonal frequency division multiplexing signals.

In an embodiment of the disclosure, the server is further configured to perform the following operation. A first difference operation is performed according to the first result to obtain a first difference. A ratio of the first difference to the second accumulated value is calculated to generate the first processed signal.

In an embodiment of the disclosure, the server is further configured to perform the following operation. Low-pass filtering is performed on the first radar signal to obtain the first processed signal.

In an embodiment of the disclosure, the vital sign includes a time-varying signal indicating a position change.

A detection method of a vital sign of the disclosure is adapted for a powered vehicle, including the following operation. A first radio frequency (RF) signal is transmitted and a first radar signal corresponding to the first RF signal is received by a first radar, in which the first RF signal includes a first transmitting in-phase component and a first transmitting quadrature component. IQ-demodulation is performed on the first radar signal to obtain a first receiving in-phase component and a first receiving quadrature component. A first convolution operation is performed to the first receiving in-phase component and a first symbol corresponding to the first transmitting quadrature component, and a first multiply accumulate (MAC) operation is performed to a first result of the first convolution operation to obtain a first accumulated value. A second convolution operation is performed to the first receiving quadrature component and the first symbol corresponding to the first transmitting quadrature component, and a second MAC operation is performed to a second result of the second convolution operation to obtain a second accumulated value. A first processed signal is generated according to the first accumulated value and the second accumulated value. A vital sign corresponding to the first radar is generated according to the first processed signal, and the vital sign is output, in which the first symbol of the first transmitting quadrature component is orthogonal to a transmitting in-phase symbol of the first transmitting in-phase component, and the first symbol is a symbol whose mean value is zero.

In an embodiment of the disclosure, the detection method further includes the following operation. A second radio frequency signal is transmitted and a second radar signal corresponding to the second radio frequency signal is received by the second radar. Preprocessing is performed on the second radar signal to obtain a second processed signal. A vital sign is generated according to the first processed signal and the second processed signal.

In an embodiment of the disclosure, the detection method further includes the following operation. In response to a first power component of the first processed signal being greater than a threshold and a second power component of the second processed signal being less than or equal to the threshold, the second processed signal is subtracted from the first processed signal to obtain the vital sign corresponding to the first radar.

In an embodiment of the disclosure, the detection method further includes the following operation. Dashboard information is automatically obtained from the powered vehicle, and a lookup table is queried according to the dashboard information to obtain a vibration frequency. The first processed signal is processed according to the vibration frequency to obtain the vital sign.

In an embodiment of the disclosure, the dashboard information includes engine speed.

In an embodiment of the disclosure, the first symbol of the first transmitting quadrature component of the first radio frequency signal and a second symbol of a second transmitting quadrature component of a second radio frequency signal are orthogonal to each other.

In an embodiment of the disclosure, the first radio frequency signal and the second radio frequency signal are orthogonal frequency division multiplexing signals.

In an embodiment of the disclosure, generating the first processed signal according to the first accumulated value and the second accumulated value includes the following operation. A first difference operation is performed according to the first result to obtain a first difference. A ratio of the first difference to the second accumulated value is calculated to generate the first processed signal.

In an embodiment of the disclosure, the detection method further includes the following operation. Low-pass filtering is performed on the first radar signal to obtain the first processed signal.

In an embodiment of the disclosure, the vital sign includes a time-varying signal indicating a position change.

Based on the above, the detection system of the disclosure may improve the accuracy of the vital sign measured by radar in an unstable environment.

DETAILED DESCRIPTION OF DISCLOSED EMBODIMENTS

In order to make the content of the disclosure easier to understand, the following specific embodiments are illustrated as examples of the actual implementation of the disclosure. In order to make the content of the disclosure easier to understand, the following specific embodiments are illustrated as examples of the actual implementation of the disclosure.

Figure 1:
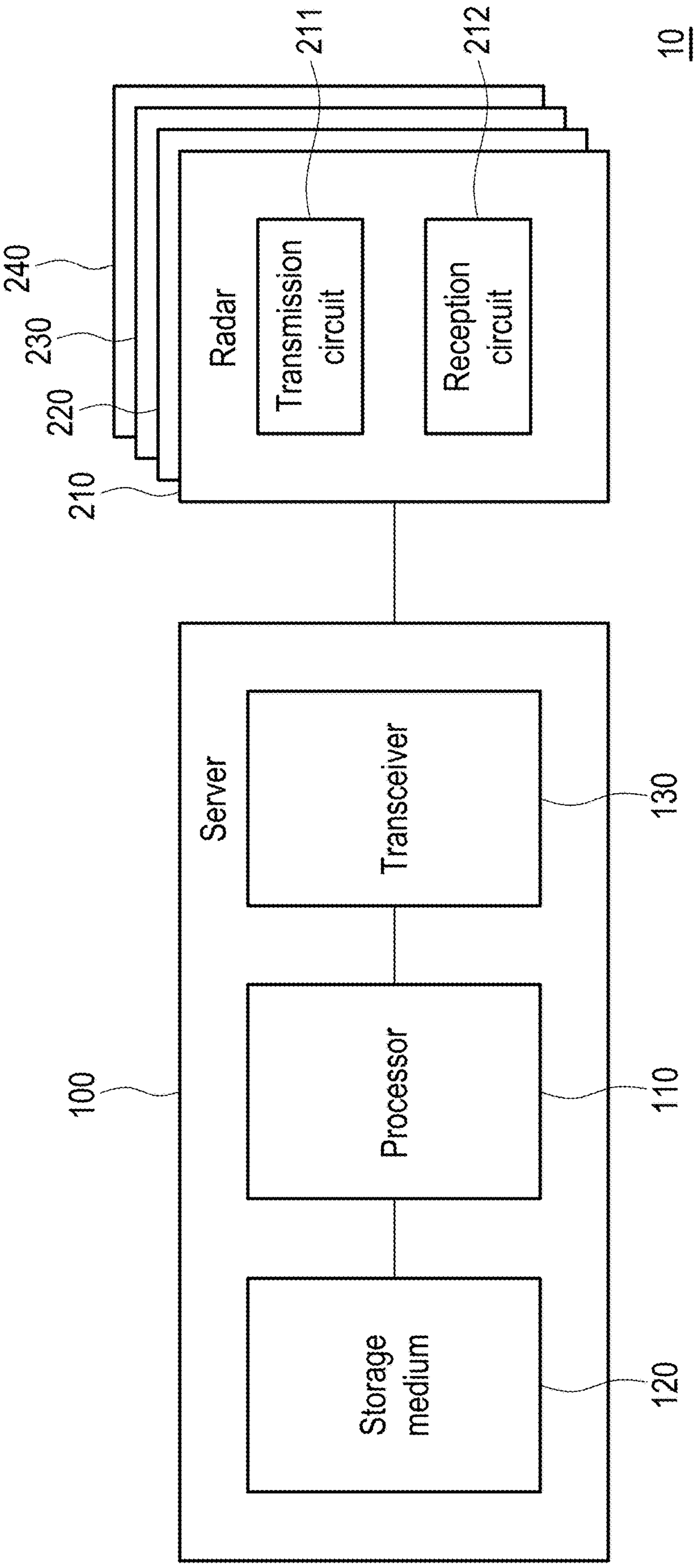
FIG. 1 is a schematic diagram of a detection system of a vital sign according to an embodiment of the disclosure.

FIG. 1 is a schematic diagram of a detection system 10 of a vital sign according to an embodiment of the disclosure. The detection system 10 may include a server 100 and i radars communicatively connected to the server 100, where i is any positive integer. In the following description, N is assumed to be 4, and the i radars may include the radar 210, the radar 220, the radar 230, and the radar 240. The radar 210, radar 220, radar 230, or radar 240 may have the same or similar configuration or function. The detection system 10 may be configured to detect the vital signs of the target, in which the vital signs may include but not limited to respiration or heartbeat.

The server 100 may include a processor 110, a storage medium 120, and a transceiver 130. The processor 110 is, for example, a central processing unit (CPU), or other programmable general-purpose or special-purpose micro control unit (MCU), microprocessor, digital signal processor (DSP), programmable controller, application specific integrated circuit (ASIC), graphics processing unit (GPU), image signal processor (ISP), image processing unit (IPU), arithmetic logic unit (ALU), complex programmable logic device (CPLD), field programmable gate array (FPGA), or other similar elements, or a combination of the elements thereof. The processor 110 may be coupled to the storage medium 120 and the transceiver 130, and access and execute multiple modules and various application programs stored in the storage medium 120.

The storage medium 120 is, for example, any type of fixed or removable random access memory (RAM), read-only memory (ROM), flash memory, hard disk drive (HDD), solid state drive (SSD), or similar elements, or a combination of the elements thereof configured to store multiple modules or various applications executable by the processor 110.

The transceiver 130 transmits or receives signals in a wireless or wired manner. The transceiver 130 may also perform operations such as low noise amplification, impedance matching, frequency mixing, up or down frequency conversion, filtering, amplification, and the like.

The radar 210 may include a transmission circuit 211 and a reception circuit 212. The radar 210 may transmit a radio frequency signal to the target through the transmission circuit 211, and may receive a radar signal corresponding to the radio frequency signal through the reception circuit 212 (i.e., a reflected signal of the radio frequency signal transmitted to the target). The radar 220, the radar 230, or the radar 240 may have the same or similar configuration or function as the radar 210.

Figure 2A:
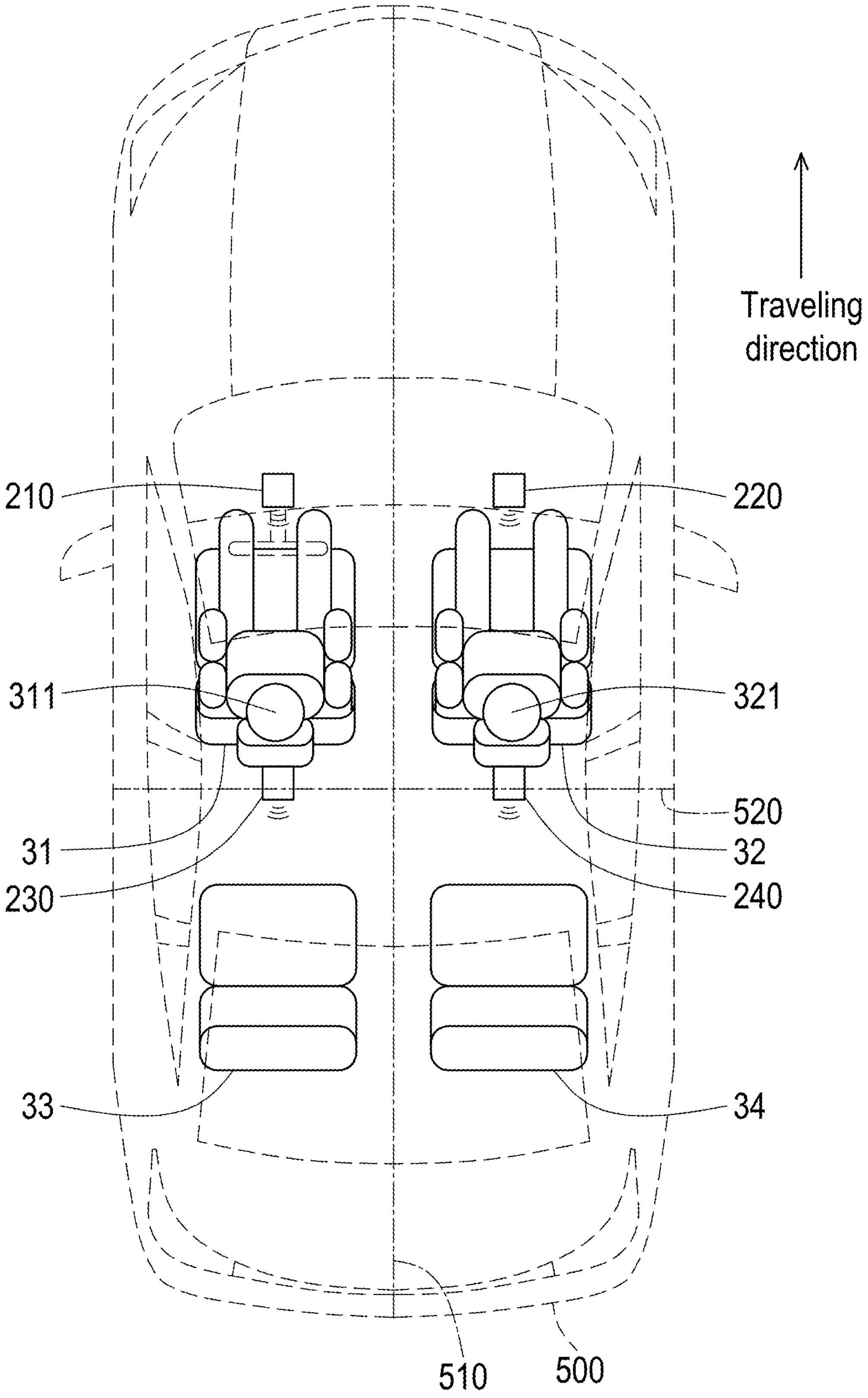
FIG. 2A and FIG. 2B are schematic diagrams of a powered vehicle according to an embodiment of the disclosure.
Figure 2B:
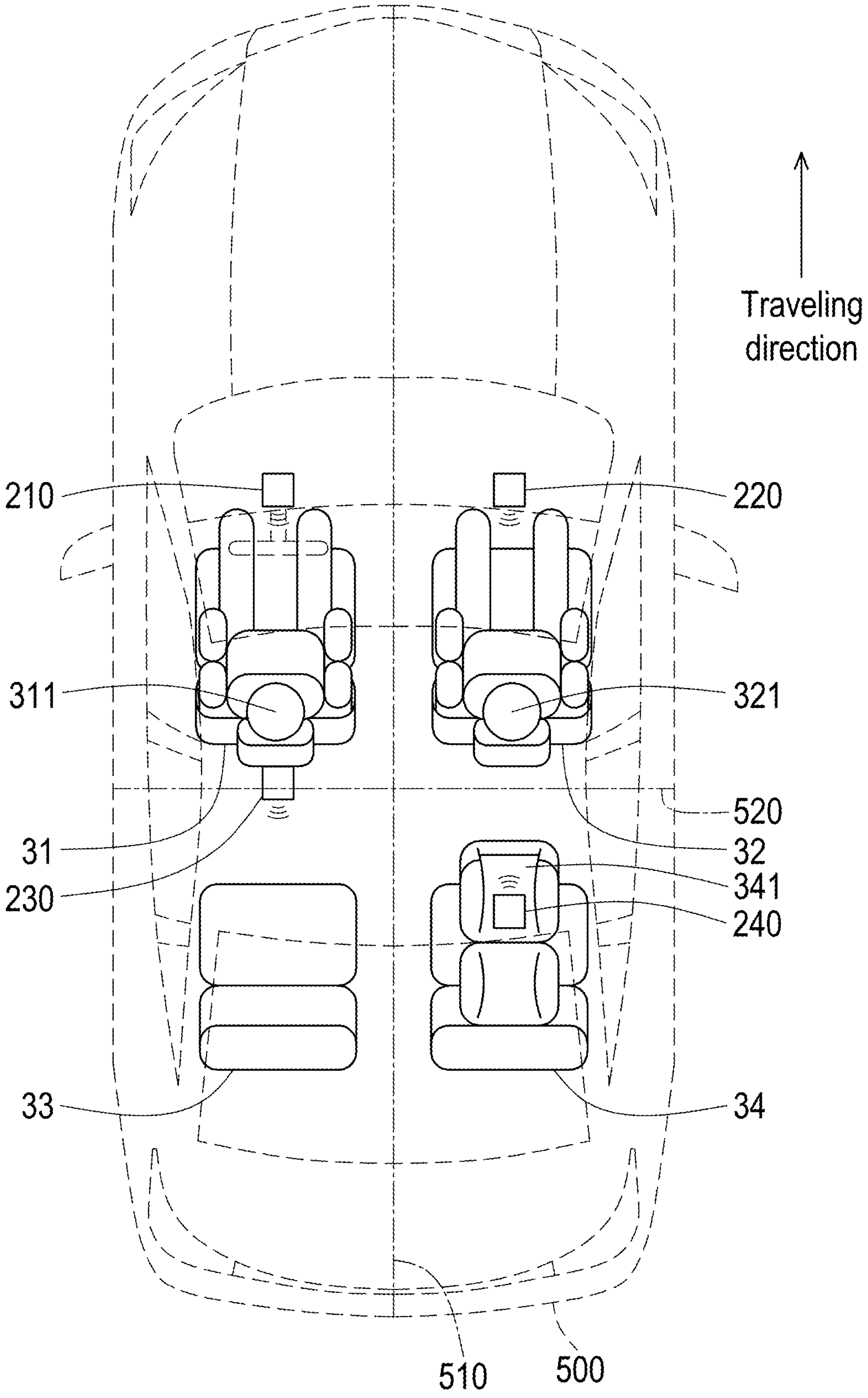

Radar may be disposed in a powered vehicle to transmit and receive wireless signals to targets in the powered vehicle. When the detection system 10 includes multiple radars, the multiple radars may be configured to respectively measure multiple different targets. FIG. 2A and FIG. 2B are schematic diagrams of a powered vehicle 500 according to an embodiment of the disclosure. The radar 210, the radar 220, the radar 230, and the radar 240 may be respectively disposed at different positions in the powered vehicle 500. Taking FIG. 2A as an example, the radar 210 may be disposed on the dashboard or the upper edge of the front windshield (i.e., the junction of the front windshield and the roof) to detect the target on the seat 31 (i.e., the driver seat) (e.g., the target 311), the radar 220 may be disposed on the upper edge of the front windshield to detect the target (e.g., the target 321) on the seat 32 (i.e., the passenger seat), the radar 230 may be disposed on the back of the driver seat to detect the target on the seat 33, and the radar 240 may be disposed on the back of the passenger seat to detect the target on the seat 34. In fact, the configuration of the radar in the powered vehicle depends on actual requirements, which is not limited in this disclosure. That is, the position of the radar may include any position in the powered vehicle and is not limited by the drawings of this disclosure. For example, when the rear passenger to be detected is a toddler or an infant in a rear-facing safety seat, one or more of the radars may be disposed on the ceiling or the upper edge of the rear window above the rear seat of the compartment of the powered vehicle, and facing the safety seat, such as the radar 240 and the safety seat 341 shown in FIG. 2B.

In one embodiment, the multiple radars of the detection system 10 may be respectively disposed at mirrored positions in the powered vehicle 500. For example, the radar 210 and the radar 220 may be respectively disposed at the relative positions of the longitudinal centerline 510 of the powered vehicle 500, the radar 230 and the radar 240 may be respectively disposed at the relative positions of the longitudinal centerline 510 of the powered vehicle 500, the radar 210 and the radar 230 may be respectively disposed at relative positions to the lateral centerline 520 of the powered vehicle 500, and the radar 220 and the radar 240 may be respectively disposed at relative positions to the lateral centerline 520 of powered vehicle 500.

Figure 3:
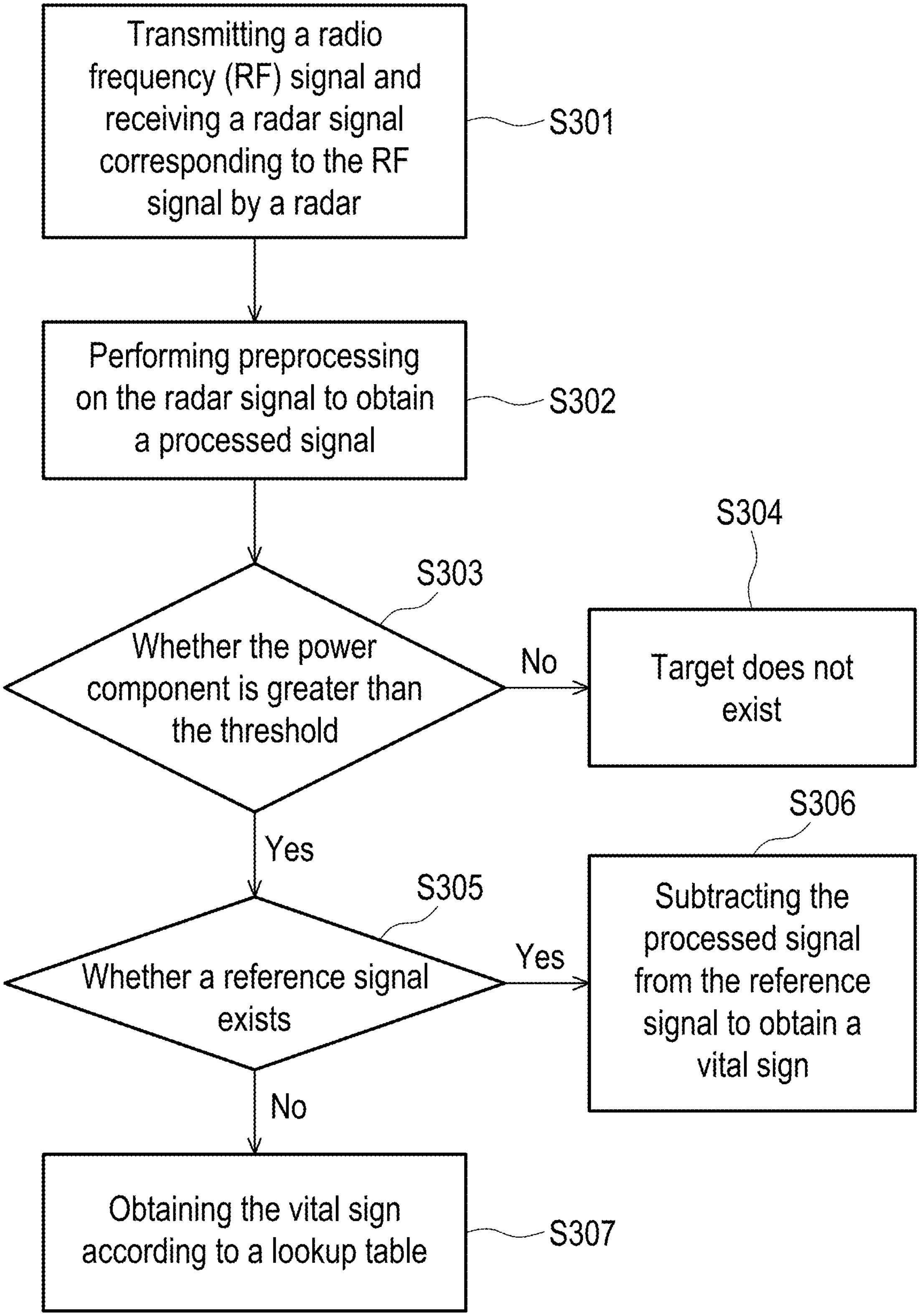
FIG. 3 is a flowchart of a detection method of a vital sign according to an embodiment of the disclosure.

FIG. 3 is a flowchart of a detection method of a vital sign according to an embodiment of the disclosure, in which the method may be implemented by the detection system 10 shown in FIG. 1. In step S301, the server 100 may transmit a radio frequency signal through the radar 210 (and/or the radar 220, 230, or 240), and receive a radar signal corresponding to the radio frequency signal. A radio frequency signal may include a transmitting in-phase component and a transmitting quadrature component, and a radar signal may include a receiving in-phase component and a receiving quadrature component.

In one embodiment, the symbols of the transmitting quadrature components of the RF signals transmitted by different radars may be orthogonal to each other, that is, the inner product of the symbols of the transmitting quadrature components of different RF signals may be zero. Furthermore, the mean value of the symbols of the transmitting quadrature components may be zero. For example, assuming that the symbol of the transmitting quadrature component of the radio frequency signal transmitted by the radar 210 is a periodically repeated sequence [1 1 1 1 1 1 1 1], then the symbol of the transmitting quadrature component of the radio frequency signal transmitted by the radar 220 may be a periodically repeated sequence [1 1 1 1 −1 −1 −1 −1], the symbol of the transmitting quadrature component of the radio frequency signal transmitted by the radar 230 may be a periodically repeated sequence [1 1 −1 −1 1 1 −1 −1], and the symbol of the transmitting quadrature component of the radio frequency signal transmitted by the radar 240 may be a periodically repeated sequence [1 −1 1 −1 1 −1 1 −1]. The inner product of any two of sequence [1 1 1 1 1 1 1 1], sequence [1 1 1 1 −1 −1 −1 −1], sequence [1 1 −1 −1 1 1 −1 −1], and sequence [1 1 −11 −1 1 −1 1 −1] is equal to zero. In addition, the mean value of each of the sequence [1 1 1 1 1 1 1 1], the sequence [1 1 1 1 −1 −1 −1 −1], the sequence [1 1 −1 −1 1 1 −1 −1], and the sequence [1 −1 1 −1 1 −1 1 −1] is equal to zero. Accordingly, the radar 210, the radar 220, the radar 230, and the radar 240 do not interfere with each other.

Figure 4:
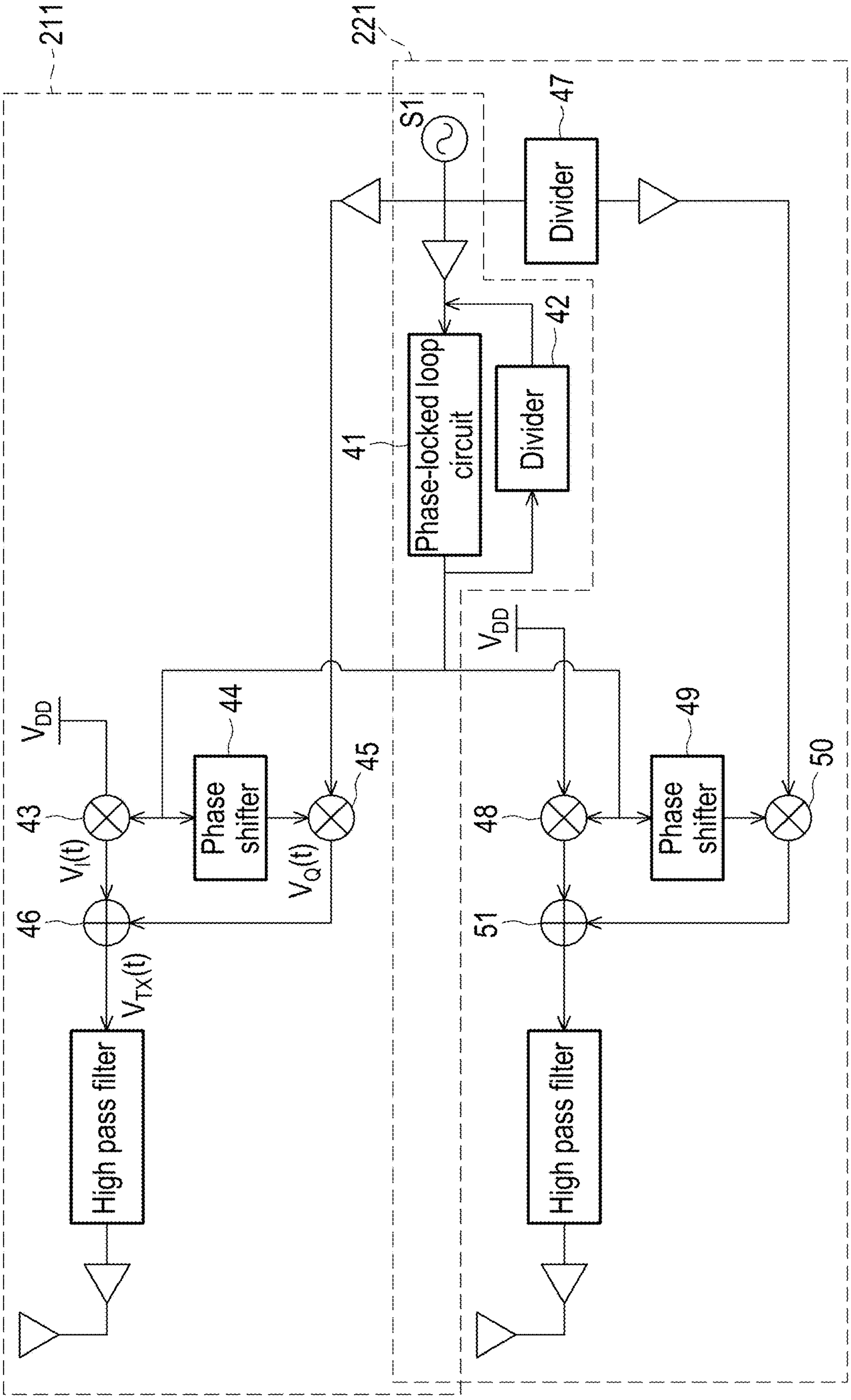
FIG. 4 is a circuit diagram of a transmission circuit of a radar according to an embodiment of the disclosure.

FIG. 4 is a circuit diagram of a transmission circuit of a radar according to an embodiment of the disclosure. It should be noted that although the transmission circuit 211 of the radar 210 and the transmission circuit 221 (not shown in FIG. 1) of the radar 220 are implemented by the same circuit in FIG. 4, the disclosure is not limited thereto. For example, the transmission circuit 211 of the radar 210 and the transmission circuit 221 of the radar 220 may also be realized by different circuits independent of each other.

The transmission circuit 211 may include a phase-locked loop circuit 41, a divider 42, a mixer 43, a phase shifter 44, a mixer 45, and an adder 46. The input terminal of the phase-locked loop circuit 41 may be coupled to a signal source for receiving a signal S1. The input terminal of the divider 42 may be coupled to the output terminal of the phase-locked loop circuit 41, and the output terminal of the divider 42 may be coupled to the input terminal of the phase-locked loop circuit 41. The frequency of the signal output by the phase-locked loop circuit 41 may be j times the frequency of the signal S1, where j is a positive integer.

The two input terminals of the mixer 43 are respectively coupled to the high potential voltage source $V_{DD}$ and the output terminal of the phase-locked loop circuit 41. The input terminal of the phase shifter 44 may be coupled to the output terminal of the phase-locked loop circuit 41. The two input terminals of the mixer 45 are respectively coupled to the signal source of the periodically oscillating signal S1 and the output terminal of the phase shifter 44. The two input terminals of the adder 46 may be respectively coupled to the output terminal of the mixer 43 and the output terminal of the mixer 45. In one embodiment, the symbol of the signal S1 may be orthogonal to the symbol of the voltage source $V_{DD}$, and the mean value of the symbol of the signal S1 may be zero. For example, if the voltage source $V_{DD}$ may be regarded as a periodically repeated sequence [1 1], then the symbol of the signal S1 may be regarded as a periodically repeated sequence [1 −1].

The output terminal of the adder 46 may be coupled to a high-pass filter and an antenna to output a radio frequency signal $V_{TX}(t)$, as shown in Formula (1), where $V_I(t)$ represents the time-varying value of the transmitting in-phase component output by the mixer 43 (or referred to as the transmitting in-phase symbol), $V_Q(t)$ represents the time-varying value of the transmitting quadrature component output by the mixer 45 (or referred to as the transmitting quadrature symbol), and $\omega_{LO}$ represents the frequency of the local oscillator. $V_I(t)$ and $V_Q(t)$ may be orthogonal to each other, and the mean value of $V_I(t)$ or $V_Q(t)$ may be zero.

$$V_{TX}(t)=V_I(t)\cos(\omega_{LO}t)+V_Q(t)\sin(\omega_{LO}t) \tag{1}$$

Taking the radar 210 as an example, after the transmission circuit 211 of the radar 210 transmits the radio frequency signal $V_{TX}(t)$ to the target, the reception circuit 212 of the radar 210 may receive the radar signal $V_{RX}(t)$ corresponding to the radio frequency signal $V_{TX}(t)$, as shown in the Formula (2), where a represents the attenuation of the radio frequency signal $V_{TX}(t)$, $\varphi_{OBJ}$ represents the phase difference caused by reflection, and D represents the distance between the radar 210 and the target (e.g., the seat 31 or the target 311). Formula (2) may be approximated to Formula (3), where $d_0$ may represent a constant portion of distance D, and d(t) may represent a moving portion of distance D.

$$V_{RX}(t)=\alpha V_I\left(t-\frac{2D}{c}\right)\cos\left(\omega_{LO}\left(t-\frac{2D}{c}\right)+\varphi_{OBJ}\right)+\alpha V_Q\left(t-\frac{2D}{c}\right)\sin\left(\omega_{LO}\left(t-\frac{2D}{c}\right)+\varphi_{OBJ}\right) \tag{2}$$

$$V_{RX}(t)\cong\alpha V_I\left(t-\frac{2d_0}{c}\right)\cos\left(\omega_{LO}\left(t-\frac{2d_0}{c}\right)-\frac{4\pi d(t)}{\lambda}+\varphi_{OBJ}\right)+\alpha V_Q\left(t-\frac{2d_0}{c}\right)\sin\left(\omega_{LO}\left(t-\frac{2d_0}{c}\right)-\frac{4\pi d(t)}{\lambda}+\varphi_{OBJ}\right) \tag{3}$$

On the other hand, the transmission circuit 221 may include a phase-locked loop circuit 41, a divider 42, a divider 47, a mixer 48, a phase shifter 49, a mixer 50, and an adder 51. The input terminal of the phase-locked loop circuit 41 may be coupled to a signal source for receiving a signal S1. The input terminal of the divider 42 may be coupled to the output terminal of the phase-locked loop circuit 41, and the output terminal of the divider 42 may be coupled to the input terminal of the phase-locked loop circuit 41. The frequency of the signal output by the phase-locked loop circuit 41 may be M times the frequency of the signal S1, where M is a positive integer. The input terminal of the divider 43 may be coupled to a signal source for receiving the signal S1, and the frequency of the signal output by the output terminal of the divider 47 may be 0.5 times the frequency of the signal S1. For example, if the symbol of the signal S1 is a periodically repeated sequence [1 −1], the symbol of the signal output by the divider 47 may be a periodically repeated sequence [1 1 −1 −1].

The two input terminals of the mixer 48 are respectively coupled to the high potential voltage source $V_{DD}$ and the output terminal of the phase-locked loop circuit 41. The input terminal of the phase shifter 49 may be coupled to the output terminal of the phase-locked loop circuit 41. The two input terminals of the mixer 50 may be respectively coupled to the output terminal of the divider 47 and the output terminal of the phase shifter 49. The two input terminals of the adder 51 may be respectively coupled to the output terminal of the mixer 48 and the output terminal of the mixer 50. The output terminal of the adder 51 may be coupled to a high-pass filter and an antenna to output a radio frequency signal.

Returning to FIG. 3, in step S302, the detection system 10 may perform preprocessing on the radar signal of the radar 210 (and/or the radar 220, the radar 230, and the radar 240) to obtain a processed signal.

In one embodiment, the processor 110 of the server 100 may perform preprocessing on the radar signal to obtain the processed signal. Taking the radar signal $V_{RX}(t)$ received by the radar 210 as an example, first, the processor 110 may perform in-phase quadrature demodulation (IQ-demodulation) on the radar signal $V_{RX}(t)$ to obtain the receiving in-phase component $I_{RX}(t)$ and the receiving quadrature component $Q_{RX}(t)$, as shown in Formula (4) and Formula (5), where $V_I$ represents the inherent DC bias corresponding to $V_I(t)$, $V_Q$ represents the inherent DC bias corresponding to $V_Q(t)$, $A_I$ represents the gain of the receiving channel corresponding to the in-phase component, $A_Q$ represents the gain of the receiving channel corresponding to the quadrature component, and $\varphi_0$ represents the phase difference caused by the non-coherence between the local oscillator of the reception circuit 212 and the radar signal $V_{RX}(t)$. $V_I$ and $V_Q$ may be orthogonal to each other. For example, if $V_I$ is a periodically repeated sequence [1 1 1 1], then $V_Q$ may be a periodically repeated sequence [1 −1 1 −1].

$$I_{RX}(t)=V_I+A_IV_I\left(t-\frac{2d_0}{c}\right)\cos\left(\varphi_0-\frac{4\pi d(t)}{\lambda}+\varphi_{OBJ}\right)+A_IV_Q\left(t-\frac{2d_0}{c}\right)\sin\left(\varphi_0-\frac{4\pi d(t)}{\lambda}+\varphi_{OBJ}\right) \tag{4}$$

$$Q_{RX}(t)=V_Q-A_QV_I\left(t-\frac{2d_0}{c}\right)\sin\left(\varphi_0-\frac{4\pi d(t)}{\lambda}+\varphi_{OBJ}\right)+A_QV_Q\left(t-\frac{2d_0}{c}\right)\cos\left(\varphi_0-\frac{4\pi d(t)}{\lambda}+\varphi_{OBJ}\right) \tag{5}$$

Next, the processor 110 may perform a convolution operation on the receiving in-phase component $I_{RX}(t)$ and $V_Q(t)$, and perform a multiply accumulate (MAC) operation on the operation result of the convolution operation to obtain an accumulated value $I_{RX}(n)$, as shown in Formula (6), where T represents the time interval between symbol changes. For example, if $V_Q$ is a sequence [1 −1], then the value of $V_Q$ changes from "1" to "−1" after the time interval T. On the other hand, the processor 110 may perform a convolution operation on the receiving quadrature component $Q_{RX}(t)$ and $V_Q(t)$, and perform a MAC operation on the operation result of the convolution operation to obtain an accumulated value $Q_{RX}(n)$, as shown in Formula (7).

$$I_{RX}(n)\cong\alpha A_I\sum_{k=0}^{N}\sin\left(\varphi_0-\frac{4\pi d(nT-kT)}{\lambda}+\varphi_{OBJ}\right) \tag{6}$$

$$Q_{RX}(n)\cong\alpha A_Q\sum_{k=0}^{N}\sin\left(\varphi_0-\frac{4\pi d(nT-kT)}{\lambda}+\varphi_{OBJ}\right) \tag{7}$$

Then, the processor 110 may perform a difference operation (e.g., a moving difference operation) on the operation result of the convolution operation of the receiving in-phase component $I_{RX}(t)$ and $V_Q(t)$ to obtain the difference $\Delta I_{RX}(n)$, as shown in Formula (8). On the other hand, the processor 110 may perform a difference operation (e.g., a moving difference operation) on the operation result of the convolution operation of the receiving quadrature component $Q_{RX}(t)$ and $V_Q(t)$ to obtain the difference $\Delta Q_{RX}(n)$, as shown in Formula (9).

$$\Delta I_{RX}(n)\cong\alpha A_I\sum_{k=0}^{N}\cos\left(\varphi_0-\frac{4\pi d(nT-kT)}{\lambda}+\varphi_{OBJ}\right)\frac{-4\pi}{\lambda}\frac{\Delta d}{T} \tag{8}$$

$$\Delta Q_{RX}(n)=-\alpha A_Q\sum_{k=0}^{N}\sin\left(\varphi_0-\frac{4\pi d(nT-kT)}{\lambda}+\varphi_{OBJ}\right)\frac{-4\pi}{\lambda}\frac{\Delta d}{T} \tag{9}$$

The processor 110 may calculate the ratio of the difference $\Delta I_{RX}(n)$ to the accumulated value $Q_{RX}(n)$, as shown in Formula (10). The processor 110 may calculate the ratio of the difference $\Delta Q_{RX}(n)$ to the accumulated value $I_{RX}(n)$, as shown in Formula (11). The processor 110 may process Formula (10), Formula (11), or Formula (12) of the multiplication product thereof to generate the processed signal PS1.

$$\frac{\Delta I_{RX}(n)}{Q_{RX}(n)} = \frac{-4\pi}{\lambda}\frac{A_I \Delta d}{A_Q T} \tag{10}$$

$$\frac{\Delta Q_{RX}(n)}{I_{RX}(n)} = \frac{4\pi}{\lambda}\frac{A_Q \Delta d}{A_I T} \tag{11}$$

$$\frac{\Delta I_{RX}(n)}{Q_{RX}(n)}\frac{\Delta Q_{RX}(n)}{I_{RX}(n)} = \frac{-16\pi}{\lambda^2}\frac{\Delta d^2}{T^2} \tag{12}$$

As mentioned above, Formula (10) or Formula (11) is substantially the time-varying rate (or rate) of the distance between the target and the radar. Formula (10) is accumulated in time sequence or Formula (11) is accumulated in time sequence to obtain the relationship between the distance and time of the target relative to the radar, and the value obtained after the accumulation may serve as the processed signal PS1. In addition, the relationship between the distance and time of the target relative to the radar may also be obtained by accumulating the square root of the absolute value of Formula (12) in time sequence. Using Formula (12) may further remove the $A_I$ (i.e., the gain of the receiving channel corresponding to the in-phase component) and $A_Q$ (i.e., the gain of the receiving channel corresponding to the quadrature component) in Formula (10) or Formula (11). This solves the issue of the inconsistency between the rate of change of $A_I$ (i.e., the degree of change in $A_I$ over time) and the rate of change of $A_Q$ (i.e., the degree of change in $A_Q$ over time).

The processor 110 may generate the processed signal PS2, the processed signal PS3, and the processed signal PS4 respectively corresponding to the radar 220, the radar 230, and the radar 240 in a manner similar to that of generating the processed signal PS1 corresponding to the radar 210.

In one embodiment, during the preprocessing of the radar signal by the processor 110, the processor 110 may perform low-pass filtering on the radar signals to filter out signals that are not related to heartbeat or respiration (e.g., noise caused by vibrations of the powered vehicle 500), thereby obtaining a processed signal. For example, the processor 110 may apply moving average filtering of X samples to the radar signal to obtain the processed signal. The processor 110 may perform moving average filtering based on the following design parameters: 3 dB frequency=5 Hz; zero frequency=12 Hz; and sampling frequency=12*X Hz.

Figure 5:
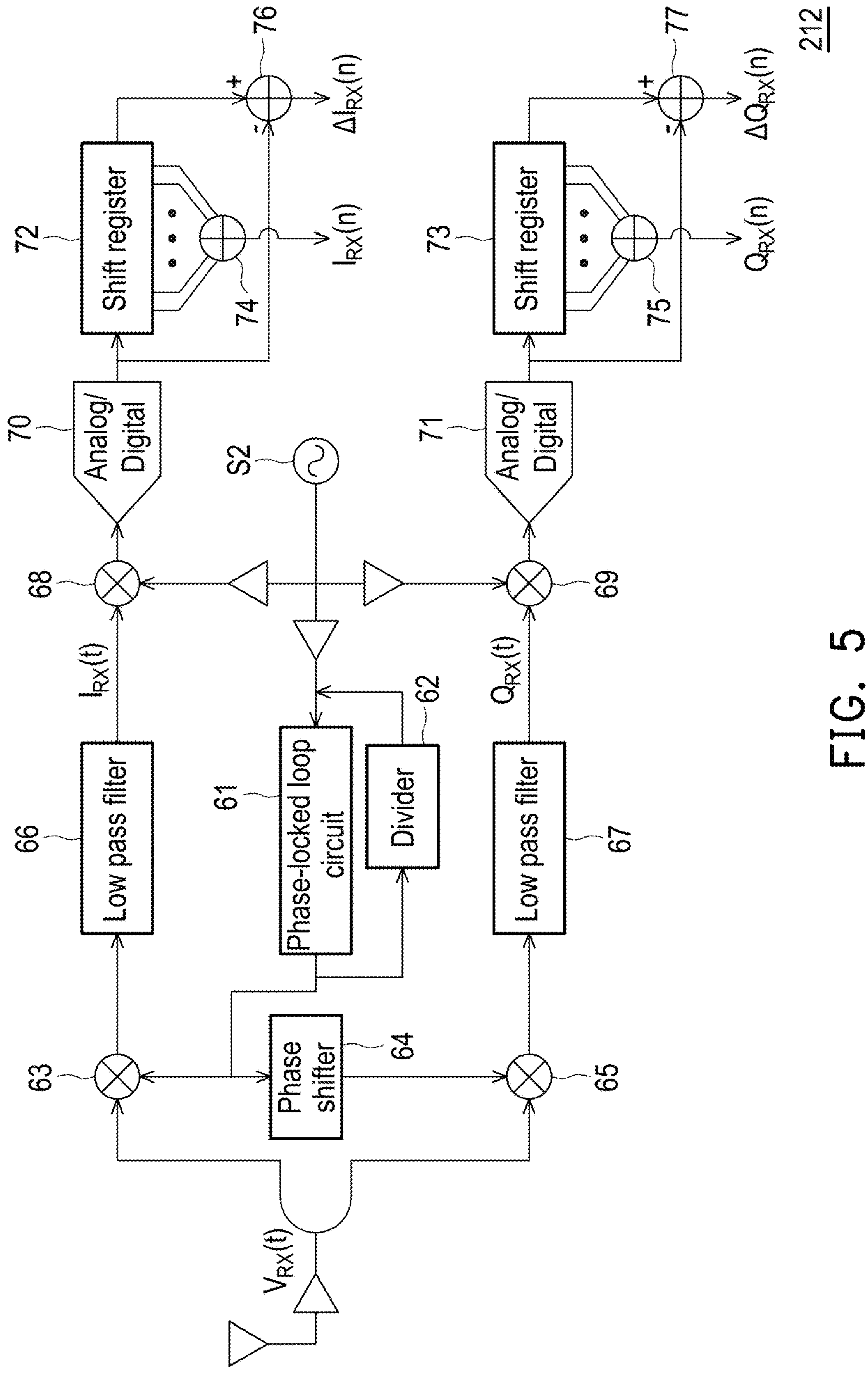
FIG. 5 is a circuit diagram of a reception circuit of a radar according to an embodiment of the disclosure.

In one embodiment, the reception circuit of the radar may perform preprocessing on the radar signal to obtain the processed signal. Taking the radar 210 as an example, FIG. 5 is a circuit diagram of a reception circuit 212 of a radar 210 according to an embodiment of the disclosure. The reception circuit 212 may perform preprocessing on the radar signal $V_{RX}(t)$ to obtain a processed signal. The reception circuit 212 may include a phase-locked loop circuit 61, a divider 62, a mixer 63, a phase shifter 64, a mixer 65, a low-pass filter 66, a low-pass filter 67, a mixer 68, a mixer 69, an analog-to-digital converter 70, an analog-to-digital converter 71, a serial-in parallel-out (SIPO) shift register 72, a serial-in-parallel-out shift register 73, an adder 74, an adder 75, a subtractor 76, and a subtractor 77.

The input terminal of the phase-locked loop circuit 61 may be coupled to a signal source for receiving the periodically oscillating signal S2. In one embodiment, the symbol of the signal S2 may be the same as the symbol of the transmitting quadrature component (i.e., $V_Q$) of the radio frequency signal $V_{TX}(t)$. The input terminal of the divider 62 may be coupled to the output terminal of the phase-locked loop circuit 61, and the output terminal of the divider 62 may be coupled to the input terminal of the phase-locked loop circuit 61. The frequency of the signal output by the phase-locked loop circuit 61 may be j times the frequency of the signal S2, where j is a positive integer.

The two input terminals of the mixer 63 may be respectively coupled to the output terminal of the phase-locked loop circuit 61 and the signal source of the radar signal $V_{RX}(t)$ (e.g., the antenna unit of the reception circuit 212). The output terminal of the mixer 63 may be coupled to the input terminal of the low-pass filter 66. The input terminal of the phase shifter 64 may be coupled to the output terminal of the phase-locked loop circuit 61. The two input terminals of the mixer 65 are respectively coupled to the signal source of the radar signal $V_{RX}(t)$ and the output terminal of the phase shifter 64. The output terminal of the mixer 65 may be coupled to the input terminal of the low-pass filter 67. After the radar signal $V_{RX}(t)$ passes through the mixer 63 and the low-pass filter 66, the radar signal $V_{RX}(t)$ may be converted into a receiving in-phase component $I_{RX}(t)$ as shown in Formula (4). On the other hand, after the radar signal $V_{RX}(t)$ passes through the mixer 65 and the low-pass filter 67, the radar signal $V_{RX}(t)$ may be converted into the receiving quadrature component $Q_{RX}(t)$ as shown in Formula (5).

The two input terminals of the mixer 68 may be respectively coupled to the output terminal of the low-pass filter 66 and the signal source of the signal S2, and the output terminal of the mixer 68 may be coupled to the input terminal of the analog-to-digital converter 70. The input terminal of the shift register 72 may be coupled to the output terminal of the analog-to-digital converter 70, and multiple output terminals of the shift register 72 may be coupled to the adder 74 to output parallel data to the adder 74. The reception circuit 212 may perform a convolution operation on the receiving in-phase component $I_{RX}(t)$ and $V_Q$ through the mixer 68. After the operation result of the convolution operation is converted into a digital signal by the analog-to-digital converter 70, the shift register 72 and the adder 74 may perform a MAC operation on the operation result to obtain an accumulated value $I_{RX}(n)$ as shown in Formula (6). On the other hand, the two input terminals of the subtractor 76 may be respectively coupled to the input terminal of the shift register 72 and the last output terminal of the shift register 72 (e.g., the output of the last stage of the shift register 72, in which the data stored in the last stage is the data that has been delayed the longest before being output in the shift register 72). The reception circuit 212 may perform a difference operation on the operation result of the convolution operation through the subtractor 76 to obtain the difference $\Delta I_{RX}(n)$ shown in Formula (8).

On the other hand, the two input terminals of the mixer 69 may be respectively coupled to the output terminal of the low-pass filter 66 and the signal source of the signal S2, and the output terminal of the mixer 69 may be coupled to the input terminal of the analog-to-digital converter 71. The input terminal of the shift register 73 may be coupled to the output terminal of the analog-to-digital converter 71, and multiple output terminals of the shift register 73 may be coupled to the adder 75 to output parallel data to the adder 75. The reception circuit 212 may perform a convolution operation on the receiving quadrature component $Q_{RX}(t)$ and $V_Q$ through the mixer 69. After the operation result of the convolution operation is converted into a digital signal by the analog-to-digital converter 71, the shift register 73 and the adder 75 may perform a MAC operation on the operation result to obtain an accumulated value $Q_{RX}(n)$ as shown in Formula (7). On the other hand, the two input terminals of the subtractor 77 may be respectively coupled to the input terminal of the shift register 73 and the last output terminal of the shift register 73 (e.g., the output of the last stage of the shift register 73, in which the data stored in the last stage is the data that has been delayed the longest before being output in the shift register 73). The reception circuit 212 may perform a difference operation on the operation result of the convolution operation through the subtractor 77 to obtain the difference $\Delta Q_{RX}(n)$ shown in Formula (9). The period of the signal S2 may be an integer multiple of the sampling period of the analog-to-digital converter 70 (or 71), and the number of bits of the shift register 72 and the shift register 73 may be an integer multiple of the ratio of the period of the signal S2 to the sampling period of the analog-to-digital converter 70 (or 71).

After obtaining the accumulated value $I_{RX}(n)$, the accumulated value $Q_{RX}(n)$, the difference $\Delta I_{RX}(n)$, and the difference $\Delta Q_{RX}(n)$, the reception circuit 212 (or the server 100) may further generate the processed signal PS1 of the radar 210 as shown in Formula (12) according to the accumulated value $I_{RX}(n)$, the accumulated value $Q_{RX}(n)$, the difference $\Delta I_{RX}(n)$, and the difference $\Delta Q_{RX}(n)$.

Returning to FIG. 3, in step S303, the processor 110 may determine whether the power component of the processed signal PS1 of the radar 210 is greater than a threshold. The power component may include the power of the processed signal PS1 within a specific frequency range (e.g., the frequency range associated with vital signs such as respiration or heartbeat: 0.25 Hz to 3 Hz). If the power component is greater than the threshold, it means that there is a target 311 sitting on the seat 31 detected by the radar 210, and the processor 110 may perform step S305. If the power component is less than or equal to the threshold, it means that there is no target sitting on the seat 31 detected by the radar 210, and the processor 110 may perform step S304. For example, the processor 110 may perform time-frequency conversion (e.g., perform Fourier transform on the processed signal) on the processed signal PS1 to generate a frequency spectrum of the processed signal PS1, and obtain the power component corresponding to a specific frequency range from the frequency spectrum. The processor 110 may determine whether the power component of the processed signal PS1 is greater than a threshold. If the processed signal PS1 is greater than the threshold, it means that a target 311 exists on the seat 31 detected by the radar 210. If the processed signal PS1 is less than or equal to the threshold, it means that a target does not exist on the seat 31 detected by the radar 210. Based on a similar method, the processor 110 may determine whether a target exists on the seat 32 detected by the radar 220, the seat 33 detected by the radar 230, or the seat 34 detected by the radar 240.

In step S304, the processor 110 may determine that a target does not exist on the seat 31 detected by the radar 210 and generate a detection result. The processor 110 may output the detection result through the transceiver 130.

In step S305, the processor 110 may determine whether a reference signal that may serve as the processed signal PS1 exists. If the reference signal exists, go to step S306. If the reference signal does not exist, go to step S307. The reference signal includes, for example, a processed signal corresponding to other radars (radars other than the radar 210, such as the radar 220, the radar 230, or the radar 240) and having a power component less than or equal to the threshold. Taking FIG. 2 as an example, since a target 321 exists on the seat 32 detected by the radar 220, the power component corresponding to the processed signal PS2 of the radar 220 is greater than the threshold. On the other hand, since a target does not exist on the seat 33 detected by the radar 230 or the seat 34 detected by the radar 240, the power component corresponding to the processed signal PS3 of the radar 230 or the power component corresponding to the processed signal PS4 of the radar 240 is less than or equal to the threshold. Accordingly, the processor 110 may determine that the processed signal PS3 or the processed signal PS4 may serve as a reference signal for the processed signal PS1, and the processed signal PS2 cannot serve as a reference signal for the processed signal PS1. If the seat 32, the seat 33, and the seat 34 are all occupied by the target, the processor 110 may determine that the reference signal for the processed signal PS1 does not exist.

In step S306, the processor 110 may subtract the reference signal (e.g., the processed signal PS3 corresponding to radar 230) from the processed signal PS1 to obtain the vital sign corresponding to the target 311 detected by the radar 210. The vital sign may include time-varying signal indicating a position change of the target 311 (e.g., movement of the chest of the target 311). The processor 110 may output the vital sign through the transceiver 130.

In step S307, the processor 110 may obtain the vital sign corresponding to the target 311 detected by the radar 210 according to a lookup table. The processor 110 may output the vital sign through the transceiver 130.

Specifically, the storage medium 120 may pre-store a lookup table corresponding to the powered vehicle 500, in which the lookup table may record the mapping relationship between the engine speed and the vibration frequency. For example, the lookup table may record that "when the engine speed of the powered vehicle 500 is 600 to 1200 revolutions per minute (RPM), the vibration frequency of the powered vehicle 500 is 10 to 20 Hz. The processor 110 may be communicatively connected to the powered vehicle 500 through the transceiver 130 to obtain dashboard information, in which the dashboard information may include the engine speed of the powered vehicle 500. The processor 110 may query the lookup table in the storage medium 120 according to the dashboard information to obtain the vibration frequency of the powered vehicle 500. After obtaining the vibration frequency, the processor 110 may process the processed signal PS1 of the radar 210 according to the vibration frequency to obtain the vital sign of the target 311. For example, the processor 110 may apply a notch filter, a low-pass filter, or other digital signal processing filter (DSP filter) to the processed signal PS1 to filter out the vibration frequency in the processed signal PS1, and then obtain the vital sign of the target 311. The notch frequency of the digital signal processing filter may be an integer multiple of the vibration frequency.

In one embodiment, the radio frequency signals transmitted by different radars (e.g., radars 210, 220, 230, and 240) are orthogonal frequency division multiplexing (OFDM) signals.

Figure 6:
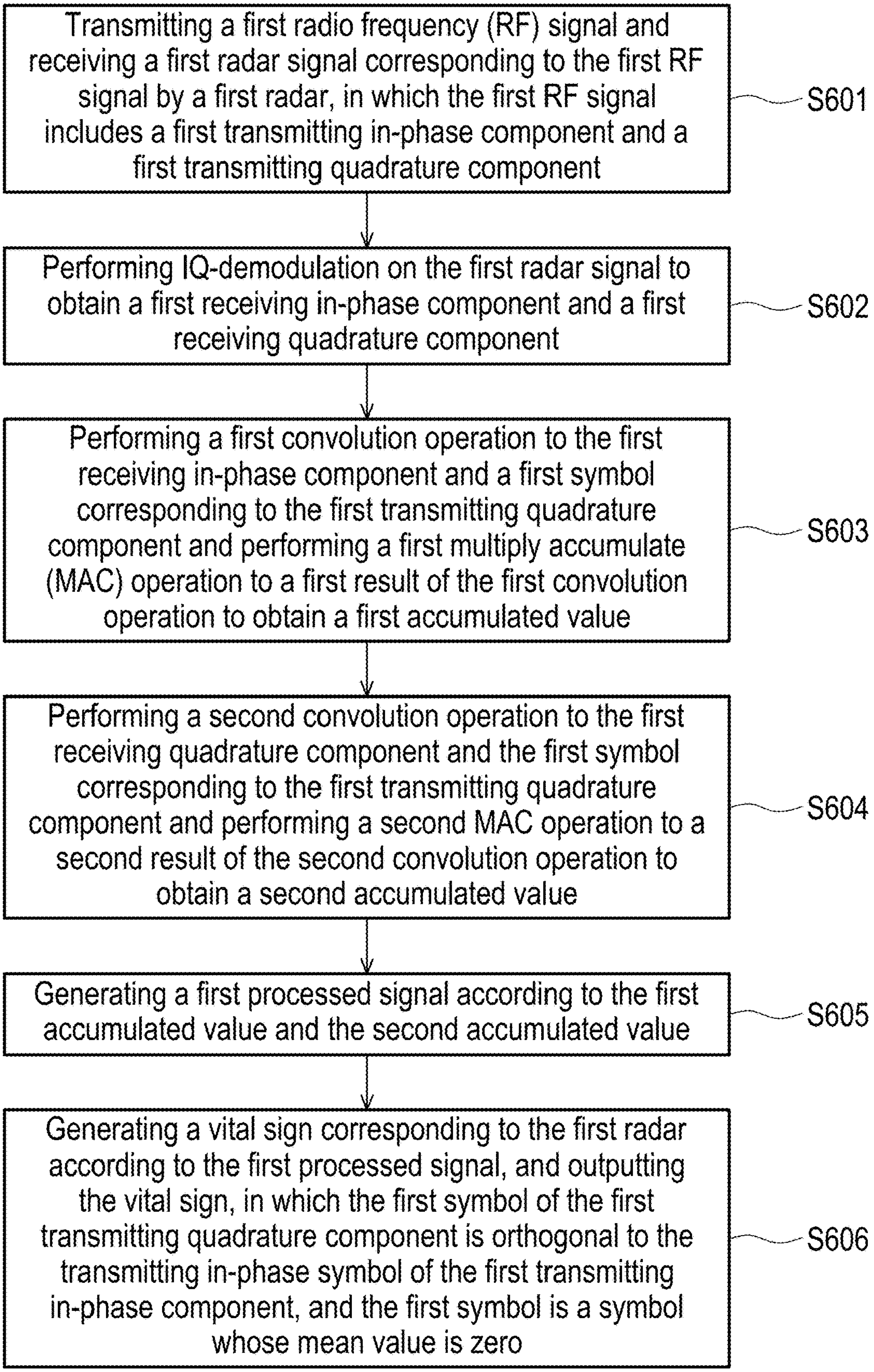
FIG. 6 is a flowchart of a detection method of a vital sign according to an embodiment of the disclosure.

FIG. 6 is a flowchart of a detection method of a vital sign according to an embodiment of the disclosure, in which the detection method is adapted for a powered vehicle and may be implemented by the detection system 10 shown in FIG.

1. In step S601, a first radio frequency (RF) signal is transmitted and a first radar signal corresponding to the first RF signal is received by a first radar, in which the first RF signal includes a first transmitting in-phase component and a first transmitting quadrature component. In step S602, IQ-demodulation is performed on the first radar signal to obtain a first receiving in-phase component and a first receiving quadrature component. In step S603, a first convolution operation is performed to the first receiving in-phase component and a first symbol corresponding to the first transmitting quadrature component, and a first multiply accumulate (MAC) operation is performed to a first result of the first convolution operation to obtain a first accumulated value. In step S604, a second convolution operation is performed to the first receiving quadrature component and the first symbol corresponding to the first transmitting quadrature component, and a second MAC operation is performed to a second result of the second convolution operation to obtain a second accumulated value. In step S605, a first processed signal is generated according to the first accumulated value and the second accumulated value. In step S606, a vital sign corresponding to the first radar is generated according to the first processed signal, and the vital sign is output, in which the first symbol of the first transmitting quadrature component is orthogonal to the transmitting in-phase symbol of the first transmitting in-phase component, and the first symbol is a symbol whose mean value is zero.

To sum up, the detection system of the disclosure may detect the seat of the powered vehicle through the radio frequency signal transmitted by the radar to obtain the detection result. The transmission circuit of the radar may use two symbols which are orthogonal to each other to generate the transmitting in-phase component and the transmitting quadrature component of the RF signal. The reception circuit of the radar may use the symbol of the transmitting quadrature component to perform steps including convolution operation and multiply accumulate operation to process the radar signal, so as to obtain the processed signal. If there are other radars in the powered vehicle that have obtained detection results that may be used as reference signals, the detection system may obtain the vital sign of the subject by comparing the processed signal with the reference signals. On the other hand, the detection system may also obtain the vital sign according to the lookup table based on the dashboard information of the powered vehicle. Compared with the traditional non-contact vital sign monitoring system, the detection system of the disclosure may accurately measure the vital sign of the subject in an unstable environment.

What is claimed is:

1. A detection system of a vital signal, adapted for a powered vehicle, comprising:

a first radar;

a second radar;

a processor, communicatively connected to the first radar and the second radar, and the processor configured to perform:

causing the first radar to transmit a first radio frequency signal and to receive a first radar signal corresponding to the first radio frequency signal, wherein the first radio frequency signal comprises a first transmitting in-phase component and a first transmitting quadrature component;

causing the second radar to transmit a second radio frequency signal and to receive a second radar signal corresponding to the second radio frequency signal;

performing in-phase quadrature demodulation on the first radar signal to obtain a first receiving in-phase component and a first receiving quadrature component;

performing a first convolution operation to the first receiving in-phase component and a first symbol corresponding to the first transmitting quadrature component, and performing a first multiply accumulate operation to a first result of the first convolution operation to obtain a first accumulated value;

performing a second convolution operation to the first receiving quadrature component and the first symbol corresponding to the first transmitting quadrature component, and performing a second multiply accumulate operation to a second result of the second convolution operation to obtain a second accumulated value;

performing a first difference operation according to the first result to obtain a first difference;

calculating a ratio of the first difference to the second accumulated value to generate a first processed signal;

performing preprocessing on the second radar signal to obtain a second processed signal; and generating a vital sign according to the first processed signal and the second processed signal, and outputting the vital sign, wherein the first symbol of the first transmitting quadrature component is orthogonal to a transmitting in-phase symbol of the first transmitting in-phase component, and the first symbol is a periodically repeated sequence, wherein the vital sign comprises a time-varying signal indicating a position change, and wherein the first radio frequency signal and the second radio frequency signal are orthogonal frequency division multiplexing signals.

2. The detection system according to claim 1, wherein the processor is further configured to perform:

in response to a first power component of the first processed signal being greater than a threshold and a second power component of the second processed signal being less than or equal to the threshold, subtracting the second processed signal from the first processed signal to obtain the vital sign corresponding to the first radar.

3. The detection system according to claim 1, wherein the processor is further configured to perform:

communicatively connected to the powered vehicle to obtain dashboard information, and querying a lookup table according to the dashboard information to obtain a vibration frequency; and filtering out the vibration frequency in the first processed signal to obtain the vital sign.

4. The detection system according to claim 3, wherein the dashboard information comprises engine speed.

5. The detection system according to claim 1, wherein the first symbol of the first transmitting quadrature component of the first radio frequency signal and a second symbol of a second transmitting quadrature component of the second radio frequency signal are orthogonal to each other.

6. The detection system according to claim 1, wherein the processor is further configured to perform:

performing low-pass filtering on the first radar signal to obtain the first processed signal.

7. A detection method of a vital signal, adapted for a powered vehicle, comprising:

causing a first radar to transmit a first radio frequency signal and to receive a first radar signal corresponding to the first radio frequency signal, wherein the first radio frequency signal comprises a first transmitting in-phase component and a first transmitting quadrature component;

causing a second radar to transmit a second radio frequency signal and to receive a second radar signal corresponding to the second radio frequency signal;

performing in-phase quadrature demodulation on the first radar signal to obtain a first receiving in-phase component and a first receiving quadrature component;

performing a first convolution operation to the first receiving in-phase component and a first symbol corresponding to the first transmitting quadrature component, and performing a first multiply accumulate operation to a first result of the first convolution operation to obtain a first accumulated value;

performing a second convolution operation to the first receiving quadrature component and the first symbol corresponding to the first transmitting quadrature component, and performing a second multiply accumulate operation to a second result of the second convolution operation to obtain a second accumulated value;

performing preprocessing on the second radar signal to obtain a second processed signal; and generating a vital sign according to a first processed signal and a second processed signal, and outputting the vital sign, wherein the first symbol of the first transmitting quadrature component is orthogonal to a transmitting in-phase symbol of the first transmitting in-phase component, and the first symbol is a periodically repeated sequence, wherein the vital sign comprises a time-varying signal indicating a position change, wherein the first radio frequency signal and the second radio frequency signal are orthogonal frequency division multiplexing signals, wherein generating the first processed signal according to the first accumulated value and the second accumulated value comprises:

performing a first difference operation according to the first result to obtain a first difference; and calculating a ratio of the first difference to the second accumulated value to generate the first processed signal.

8. The detection method according to claim 7, further comprising:

in response to a first power component of the first processed signal being greater than a threshold and a second power component of the second processed signal being less than or equal to the threshold, subtracting the second processed signal from the first processed signal to obtain the vital sign corresponding to the first radar.

9. The detection method according to claim 7, further comprising:

obtaining dashboard information from the powered vehicle, and querying a lookup table according to the dashboard information to obtain a vibration frequency; and filtering out the vibration frequency in the first processed signal to obtain the vital sign.

10. The detection method according to claim 9, wherein the dashboard information comprises engine speed.

11. The detection method according to claim 7, wherein the first symbol of the first transmitting quadrature component of the first radio frequency signal and a second symbol of a second transmitting quadrature component of the second radio frequency signal are orthogonal to each other.

12. The detection method according to claim 7, further comprising:

performing low-pass filtering on the first radar signal to obtain the first processed signal.

* * * * *